US008155886B2

(12) United States Patent
Cross et al.

(10) Patent No.: US 8,155,886 B2
(45) Date of Patent: Apr. 10, 2012

(54) AUTOMATED CLINICAL SYSTEM TO FACILITATE SECONDARY REVIEW AND AUTHENTICATION OF CLINICAL LABORATORY RESULT VALUES

(75) Inventors: Lori N. Cross, Kansas City, MO (US); Diane L. Berkowitz, Polo, MO (US); Brent W. Bossi, Smithville, MO (US); Jeffrey D. Fry, Lansing, KS (US); Timothy S. Kelly, Leawood, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 270 days.

(21) Appl. No.: 10/262,071

(22) Filed: Oct. 1, 2002

(65) Prior Publication Data

US 2004/0030578 A1    Feb. 12, 2004

Related U.S. Application Data

(60) Provisional application No. 60/401,717, filed on Aug. 7, 2002.

(51) Int. Cl.
*G01N 33/48* (2006.01)
*G01N 31/00* (2006.01)
*G06G 7/48* (2006.01)

(52) U.S. Cl. .............................. 702/19; 702/22; 703/11
(58) Field of Classification Search .................. 434/262; 435/4, 6; 705/1–4, 6
See application file for complete search history.

(56) References Cited

U.S. PATENT DOCUMENTS

| 5,841,975 | A | * | 11/1998 | Layne et al. ................... 709/203 |
| 6,177,940 | B1 | * | 1/2001 | Bond et al. ..................... 434/262 |
| 6,977,178 | B2 | * | 12/2005 | Hodge et al. .................... 436/94 |
| 2004/0078216 | A1 | * | 4/2004 | Toto .................................. 705/2 |

* cited by examiner

*Primary Examiner* — Eric S Dejong
(74) *Attorney, Agent, or Firm* — Shook Hardy & Bacon LLP (57) ABSTRACT

A method in a computer system for the review and authentication of clinical laboratory result values is provided. The method includes receiving patient data. The method also includes accessing review criteria. The method further includes comparing the patient data and the review criteria to determine if the patient data should be routed for review. The method further includes routing qualified patient data to a review hierarchy including at least one review queue defined by at least one user.

4 Claims, 7 Drawing Sheets

Result Viewer

Task  Edit  View  Help

Person Demographics — 101
Doe, John        04/03/1950
123-45-6789      Male        25, 211, A    Dx codes

Procedure — 102
01-001-000001    05/21/2002 9:56:39 RT    Dr. John Smith
                 RP6285    In-Review      |order comment|

Results: — 103

| Order | Assay | Result | Flags | Status | Prev. | Time | Ref. Range | Units |
|---|---|---|---|---|---|---|---|---|
| Chem7 | Na | 152 | H | In-Review | 149 | 19 Hours | 136-146 | mEq/L |
| Chem7 | K | 5.5 | H | In-Review | 4.4 | 19 Hours | 3.5-4.5 | mEq/L |
| Chem7 | CL | 89 | L | In-Review | 91 L | 19 Hours | 98-106 | mEq/L |
| Chem7 | CO2 | 24 |  | In-Review | 22 | 19 Hours | 22-29 | mEq/L |
| Chem7 | Gluc | 145 | H | In-Review | 165 H | 19 Hours | 65-110 | mg/dl |
| Chem7 | BUN | 31 | H | In-Review | 35 H | 19 Hours | 7-18 | mg/dl |
| Chem7 | Creat | 21 | H | In-Review | 2.3 H | 19 Hours | 0.8-1.5 | mg/dl |

Result Comment: — 104

Ready    PROD    RP6285    05/21/2002 9:57

AUTOMATED CLINICAL SYSTEM TO FACILITATE SECONDARY REVIEW AND AUTHENTICATION OF CLINICAL LABORATORY RESULT VALUES

CROSS-REFERENCE TO RELATED APPLICATIONS

This application claims the benefit of priority to provisional application No. 60/401,717 filed Aug. 7, 2002.

STATEMENT REGARDING FEDERALLY SPONSORED RESEARCH OR DEVELOPMENT

Not applicable.

TECHNICAL FIELD

The present invention relates to a computer system and, more particularly, to a computer system for providing secondary review and authentication of clinical laboratory result values.

BACKGROUND OF THE INVENTION

A number of clinical laboratory tests are oftentimes required to treat a person. Since a person's health is at stake, the reliability of the results of these tests is of great import. Accordingly, in some cases, a secondary review of the clinical laboratory result value from a particular test is desirable.

In the past, numerous approaches have been used to review and authenticate clinical laboratory result values within an automated system. Typically, a limited number of review criteria have been employed to trigger secondary review. These review criteria included limited delta checking of the clinical test result to a previous test result for the person, and specified high, low and critical ranges for particular test result values. In other cases, the service resource to which an order was to be routed (the area of the laboratory at which the work is performed) initiated a secondary review. The prior automated systems do not provide review criteria for microbiology lab results based on susceptibility results. Susceptibility results test a bacteria's susceptibility or resistance to one or more antibiotics.

The delta checking in prior systems was calculated solely by the difference between a patient's prior test result and current test result. If the difference between the two results was specified range or percentage, review would be triggered. This set range or percentage difference was inflexible and could not be changed depending on the result value, patient species, patient age or patient gender.

If patient data satisfied these limited review criteria, the data was routed to a review queue defined by the location or work area in the laboratory where the patient sample was tested. By way of example, the chemistry work area had a review queue to which only chemistry results could be routed. As such, hematology results could not be routed to the chemistry review queue.

These systems also provided limited review queue functionality. Only one user at a time could review and approve results. Further, these systems also did not provide the ability to route results to review as read only. All results required approval by the user before they were released.

SUMMARY OF THE INVENTION

Generally described, a method in a computer system for the authentication of clinical laboratory result values is provided. The method includes accessing review criteria, where the review criteria include instrument criteria, order criteria, approval criteria, result correction criteria, patient result change criteria, mandatory criteria, dilution criteria, laboratory information criteria, test specific criteria or combinations thereof. The method also includes receiving patient data, and comparing the review criteria to the patient data and determining whether the patient data qualifies for review.

In another aspect of the invention, a method in a computing environment for the authentication of microbiology clinical laboratory test results is provided. The method includes accessing microbiology test result review criteria. The method also includes receiving microbiology patient data, and comparing the review criteria to the patient data and determining whether the patient data qualifies for review.

In yet another aspect of the invention, a method in a computing environment for the authentication of clinical laboratory test results is provided. The method includes accessing review criteria and receiving patient data. The method further includes comparing the review criteria to the patient data and determining whether the patient data is to be reviewed. If the patient data is to be reviewed, the patient data is placed in a review hierarchy including at least one review queue defined by at least one user.

In still another aspect of the invention, a method in a computing environment is provided for routing clinical laboratory tests results for review. The method includes receiving patient data for review. The patient data is routed to a review hierarchy including at least one review queue defined by at least one user.

In another aspect of the invention, a method in a computing environment for triggering review of clinical laboratory test results is provided. The method includes accessing at least one criteria, such as the current patient test result, age of patient, sex of patient, species of patient, test performed and/or instrument performing test. The required numeric or percent change is then determined that will trigger review based on the criteria. The method further includes accessing the prior patient test result and subtracting the current patient test result from the prior patient test result to determine the current numeric or percent change. The current numeric or percent change is compared with the required numeric or percent change needed to determine if the patient data qualifies for review.

Additional advantages and novel features of the invention will be set forth in part in a description which follows, and in part will become apparent to those skilled in the art upon examination of the following, or may be learned by practice of the invention.

BRIEF DESCRIPTION OF THE DRAWINGS

The present invention is described in detail below with reference to the attached drawing figures, wherein:

FIG. 7 is an exemplary screen of the microbiology clinical laboratory result viewer.

DETAILED DESCRIPTION OF THE INVENTION

Figure 1:
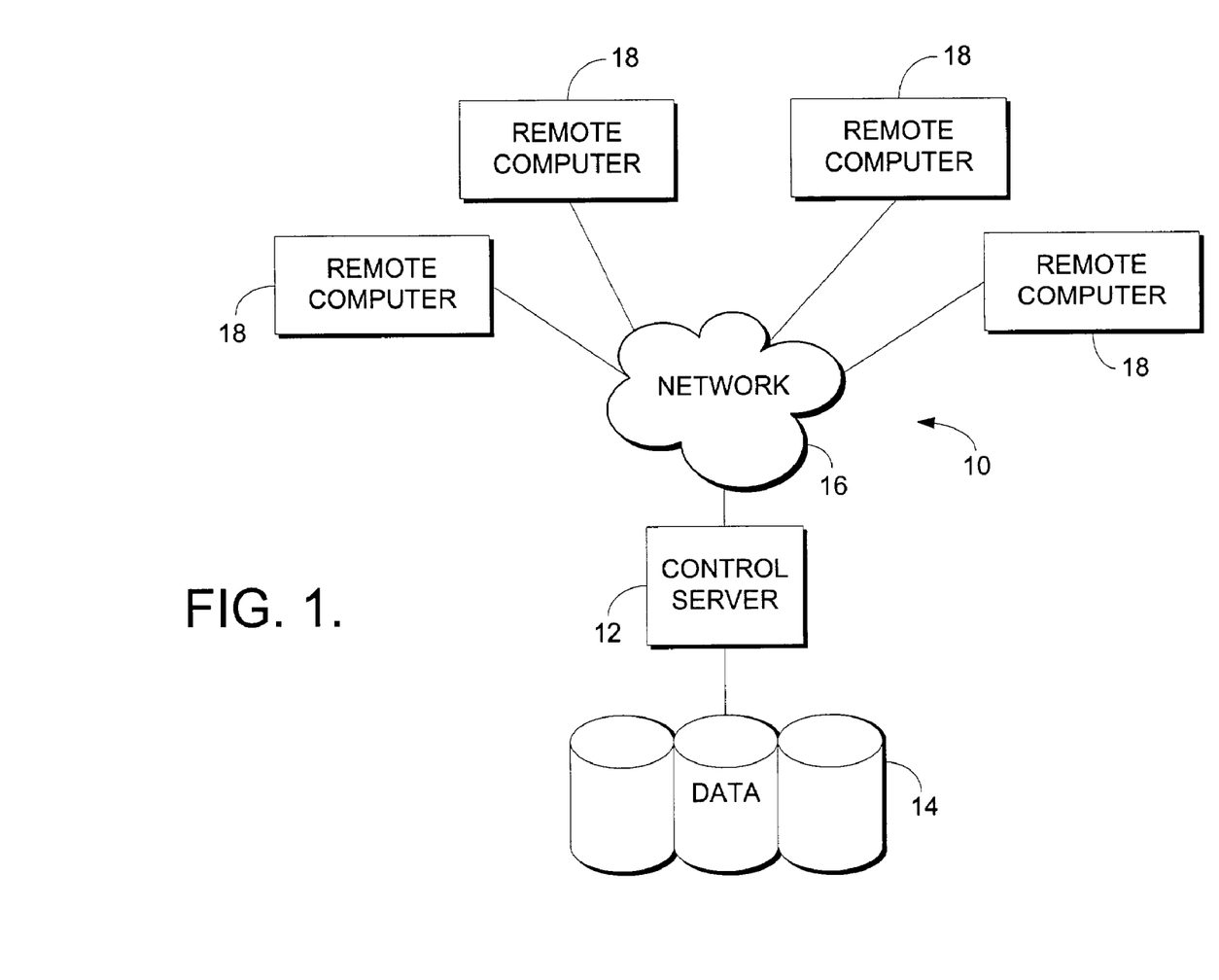
FIG. 1 is a schematic diagram of a suitable computing system environment for use in implementing the present invention.

The present invention provides a method and system for the review and validation of clinical laboratory result values. FIG. 1 illustrates an example of a suitable clinical validation computing system environment 10 on which the invention may be implemented. The clinical validation computing system environment 10 is only one example of a suitable computing environment and is not intended to suggest any limitation as to the scope of use or functionality of the invention. Neither should the computing environment 10 be interpreted as having any dependency or requirement relating to any one or combination of components illustrated in the exemplary environment 10.

The invention is operational with numerous other general purpose or special purpose computing system environments or configurations. Examples of well-known computing systems, environments, and/or configurations that may be suitable for use with the invention include, but are not limited to, personal computers, server computers, handheld or laptop devices, multiprocessor systems, microprocessor-based systems, set top boxes, programmable consumer electronics, network PCs, minicomputers, mainframe computers, distributed computing environments that include any of the above systems or devices, and the like.

The invention may be described in the general context of computer-executable instructions, such as program modules, being executed by a computer. Generally, program modules include, but are not limited to, routines, programs, objects, components, and data structures that perform particular tasks or implement particular abstract data types. The invention may also be practiced in distributed computing environments where tasks are performed by remote processing devices that are linked through a communications network. In a distributed computing environment, program modules may be located in both local and remote computer storage media, including memory storage devices.

With reference to FIG. 1, an exemplary clinical validation system for implementing the invention includes a general purpose computing device in the form of server 12. Components of server 12 may include, but are not limited to, a processing unit, internal system memory, and a suitable system bus for coupling various system components, including a database cluster 14 to the control server 12. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 12 typically includes therein or has access to a variety of computer readable media, for instance, database cluster 14. Computer readable media can be any available media that can be accessed by server 12, and includes both volatile and nonvolatile media, removable and nonremovable media. By way of example, and not limitation, computer readable media may comprise computer storage media and communication media. Computer storage media may be implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 12. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media such as acoustic, RF, infrared and other wireless media. Combinations of any of the above should also be included within the scope of computer readable media.

The computer storage media, including database cluster 14, discussed above and illustrated in FIG. 1, provide storage of computer readable instructions, data structures, program modules, and other data for server 12. Server 12 may operate in a computer network 16 using logical connections to one or more remote computers 18. Remote computers 18 can be located at a variety of locations in a medical or clinical laboratory environment, for example, but not limited to, hospitals, other inpatient settings, testing labs, medical billing and financial offices, and hospital administration. The remote computers may also be physically located in a non-traditional clinical laboratory or medical care environments so that the entire health care community is capable of integration on the network. Each remote computer 18 may be a personal computer, server, router, a network PC, an interfaced instrument, a peer device or other common network node, and may include some or all of the elements described above relative to server 12. Computer network 16 may be a local area network (LAN) and/or a wide area network (WAN), but may also include other networks. Such networking environments are commonplace in offices, enterprise-wide computer networks, intranets and the Internet. When utilized in a WAN networking environment, server 12 may include a modem or other means for establishing communications over the WAN, such as the Internet. In a networked environment, program modules or portions thereof may be stored in server 12, or database cluster 14, or on any of the remote computers 18. For example, and not limitation, various application programs may reside on the memory associated with any one or all of remote computers 18. It will be appreciated that the network connections shown are exemplary and other means of establishing a communications link between the computers may be used.

By way of example, a user may enter commands and information into server 12 or convey commands and information to the server 12 via remote computers 18 through input devices, such as keyboards or pointing devices, commonly referred to as a mouse, trackball, or touch pad. Other input devices may include accepting data from an interface or logic system, microphone, satellite dish, scanner or the like. Server 12 and/or remote computers 18 may have any sort of display device, for instance, a monitor. In addition to a monitor, server 12 and/or computers 18 may also include other peripheral output devices, such as speakers and printers.

Although many other internal components of server 12 and computers 18 are not shown, those of ordinary skill in the art will appreciate that such components and their interconnection are well known. Accordingly, additional details concerning the internal construction of server 12 and computers 18 need not be disclosed in connection with the present invention.

The method and system of the present invention includes the steps of receiving review criteria, receiving a clinical laboratory order and its result values and determining whether the result values should be reviewed. Although the method and system are described as being implemented in a WINDOWS operating system operating in conjunction with a comprehensive healthcare network, one skilled in the art would recognize that the method and system can be implemented on any system supporting the receipt and processing of review criteria and clinical laboratory orders and result values.

Figure 2:
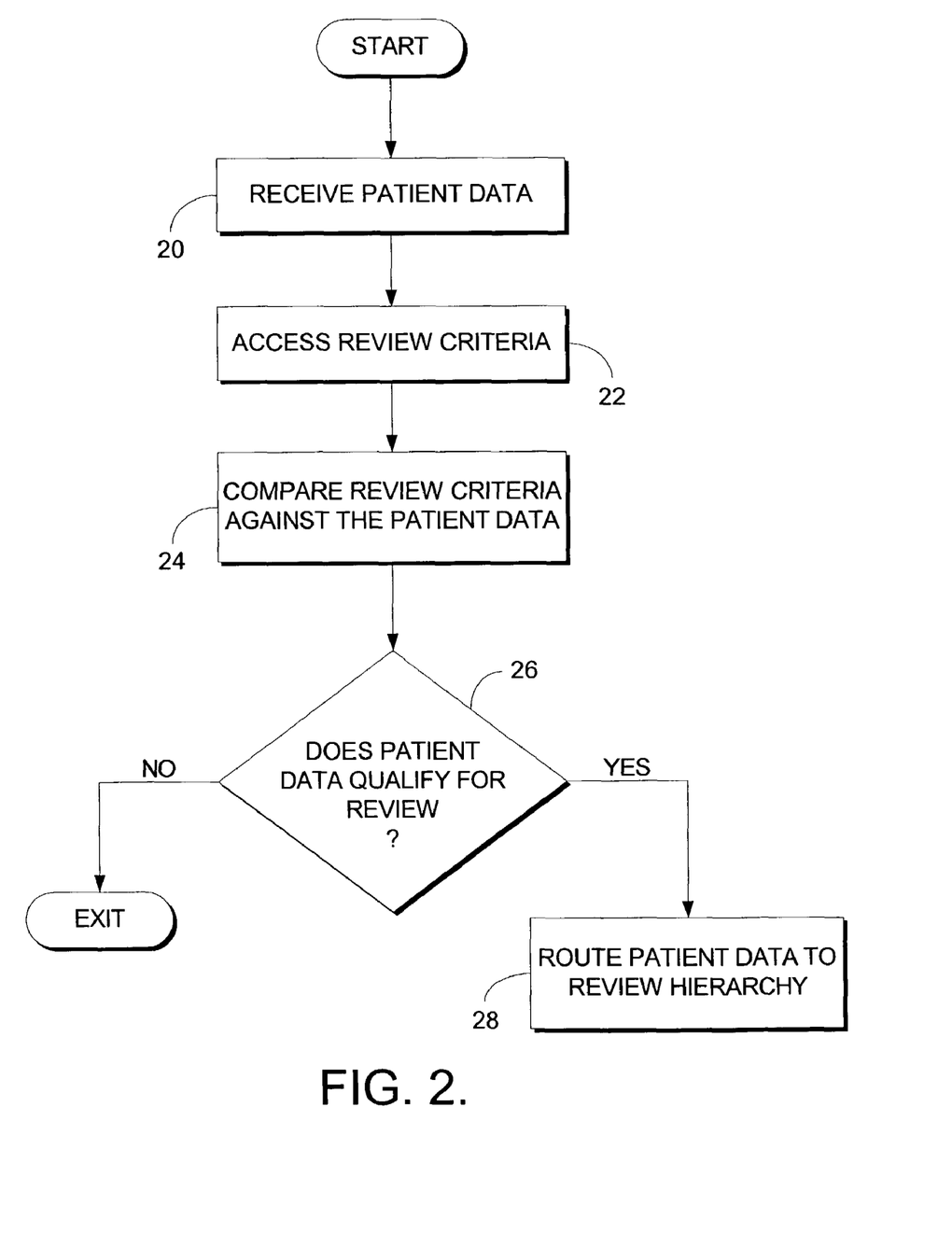
FIG. 2 is a flow diagram illustrating the overall method for the authentication of clinical laboratory test results.

With reference to FIG. 2, an overview of the system and method is described for comparing patient data against review criteria to determine whether the patient data should be reviewed. At step 20, the system receives the patient data. At step 22, the clinical validation system accesses the review criteria. The review criteria and patient data are compared in step 24. At step 26, the system determines if the patient data qualifies for review. If the patient data does not qualify for review, it is not sent for review and exists the system. If the patient data qualifies for review, the patient data is routed to a review hierarchy in step 28.

In the first step of the clinical validation system and method, patient data is received by the system at step 20. "Patient data" as used herein includes, but is not limited to, information associated with the order, patient information, genotype and phenotype information, laboratory information, result values from clinical laboratory results and miscellaneous information regarding the clinical laboratory results. One of skill in the art can appreciate that patient data can include a variety of information.

An "order" includes, but is not limited to, information associated with the order for a clinical laboratory test and includes, but is not limited to, the patient species (i.e., human vs. dog), the patient location, the ordering physician and the time of day the patient sample was taken. "Patient information" includes, but is not limited, past patient clinical laboratory results, patient medical history, patient billing information, patient gender, patient age, patient name and patient identity number. Information regarding the laboratory that performs the clinical laboratory tests may include, but is not limited to, the performing service resource (the area of the laboratory that completed the work) and the ratio of medical technologists to lab technicians. "Laboratory information" includes, but is not limited to, information regarding the laboratory staff, education of the laboratory staff and the medical technicians to staff ratio for the laboratory conducting the tests.

"Result values" include, but are not limited to, numeric and codified values depicting the results from clinical laboratory tests such as chemistry, hematology, microbiology and blood bank departmental testing. These departments analyze blood specimens and other body fluids (or tissue specimens) and typically publish discrete result values or reports. Result values or reports may also include alphabetic information indicators, reports and flags to specify particular lab result values. "Miscellaneous information" regarding clinical laboratory results includes, but is not limited to, autoverification results, dilution factors and instrument error codes.

Preferably, the order and patient test results are entered at step 20 at one of the remote computers 18 and are transmitted to the control server 12 via the network 16. Patient information and information regarding the laboratory conducting the laboratory tests may also be received at one of the remote computers 18 and transmitted to the control server 12 via the network 16. However, one of skill in the art will appreciate that patient data, such as patient information and information regarding the laboratory conducting the laboratory tests, may also be received by the system by accessing the information from tables stored in the database 14.

Once the patient data is received, the review criteria are accessed from the clinical validation system at step 22. For example, the system may access the review criteria that are maintained in the memory of the system such as in database cluster 14. The review criteria may be input into the clinical validation system by a person or persons with appropriate security. One of skill in the art will appreciate that the review criteria may be input using a variety of methods. Preferably, the review criteria are defined using database building tools and are capable of modification.

The review criteria for non-microbiology clinical laboratory tests may include such things as instrument criteria, order criteria, approval criteria, patient result change criteria, result correction criteria, mandatory criteria, dilution criteria, laboratory information criteria, test specific criteria and combinations thereof. Preferably, these criteria may be used in combination with other criteria, including but not limited to, change in result values, presence of result comments, presence of order comments, low result values, high result values and critical result values or combinations thereof. Non-microbiology clinical laboratory tests may be conducted in, but are not limited to, the following areas: chemistry, hematology, pathology, immunology and serology, toxicology, urinalysis, human leukocyte antigen (HLA) testing, virology, blood bank donor, blood bank transfusion, radiology, cardiology, and clinical testing processes. "Test specific criteria" include previous results and historical changes such as historical ABO/Rh changes.

"Instrument criteria" as used herein include the presence of an instrument error code, result values outside of linearity ranges, result values outside of feasibility ranges, autoverification failure and the service resource that performed the clinical laboratory test. Instrument error codes occur when an error is detected in the instrument conducting the test. The system may route the patient data for review based on the presence of an error code. "Linearity ranges" as used herein are between the lowest and highest measurement a laboratory instrument can measure. Result values that are higher or lower than the linearity range may be used to trigger review. "Feasibility ranges" as used herein include result values that are compatible with life. Result values that are not compatible with life may be used to trigger review. Many values that are not compatible with life are due to clerical error. Autoverification of laboratory results is a process whereby the laboratory results are automatically verified (completed and published) when the results are received from an automated instrument after the system compares information about the results received to reference data and past patient results. Results that pass the internal autoverification checks are verified by the system and released for publication via inquiries and printed patient reports. If a result value fails autoverification, this may be used to trigger review. "Performing service resource" as used herein includes the instruments or group of instruments where the clinical laboratory tests have been performed. In other words, the area of the laboratory that completed the work.

"Order criteria" as used herein include data included in an order given to perform a laboratory test including, but not limited to, patient species, patient location, ordering physician and time of day the patient sample to be tested was taken. For example, if specified as review criteria, secondary review may be triggered because a particular physician ordered the tests.

"Approval criteria" as used herein are based on the person who verifies the result values from clinical laboratory tests before the patient data is sent to the system to determine if the patient data should be routed for review. In other words, the identity of the person verifying the result values in the laboratory may be criteria used to trigger review. For example, if the person verifying the result values is a student or inexperienced technician, the patient data may be routed for secondary review.

"Result correction criteria" as used herein is a result value that is changed from the original value to a new value by the person who verifies the result values in the laboratory. The result value may be flagged as "corrected". The correction of the original value may be criteria used to trigger review.

"Patient result change criteria" as used herein includes when the system determines the numeric or percentage differential between the current patient test result value and prior patient test result value that will trigger review based upon the current patient result value, the prior patient result value patient age, patient gender, species of patient, test performed, specimen type or instrument performing the test. For example, current patient result values may be used to determine the numeric range required to trigger secondary review. Namely, a glucose test with a current patient result value of between 0-100 mg/dl (milligrams per deciliter) will trigger review if there has been a numeric change of at least five between the current patient result value and the prior patient test result value. A glucose test with a current result value of between 100-200 mg/dl will trigger review if there has been a numeric change of at least twenty between the current patient test result value and prior patient test result value. Thus, a glucose test with a current result value of 95 mg/dl and a prior result of 101 mg/dl will trigger review because the numeric change is six. On the other hand, a glucose test with a current test result value of 180 mg/dl and a prior test result value of 199 mg/dl will not trigger review because the numeric change is only nineteen.

In another example, the system may perform a "reverse check" comparing the prior patient result value to the numeric or percent change needed to trigger review. Based on the numeric ranges in the above example, a glucose test with a current result value of 102 mg/dl and a prior result value of 95 mg/dl will not qualify for review because the numeric change is only seven, and a numeric change of at least twenty is needed to trigger review. However, review will be triggered with reverse check because the prior result value is 95 mg/dl and the current result value is 102 mg/dl, and the numeric change between the current result value and the prior result value is seven.

"Mandatory criteria" as used herein refer to the automatic routing of patient data irrespective of the test results. Mandatory criteria specify particular clinical laboratory tests where the orderable item will always be routed for review. Preferably, the mandatory criteria are defined using database building tools. For example, it may be specified in the review criteria to route all test results for a Serum Protein Electrophoresis for review regardless of the information associated with the order or the test result values.

"Dilution criteria" as used herein refer to when a dilution factor is present in patient test results. The presence of a dilution factor may be used to trigger review. "Laboratory information criteria" as used herein include information regarding the laboratory staff, education of the laboratory staff and the medical technicians to staff ratio for the laboratory conducting the tests.

The review criteria for microbiology clinical laboratory tests include, but are not limited to, one of instrument criteria, order criteria, approval criteria, mandatory criteria, laboratory information criteria, microbiology specific criteria, patient result change criteria and combinations thereof.

"Microbiology test result criteria" include, but are not limited to, source, body site, susceptibility results, report responses, correlation checking failure, abnormal results, automatic no growth and procedure status (positive/negative). "Automatic no growth" is a process whereby reports for certain culture types (such as blood cultures) stating "negative" or "no growth" are automatically issued based on instrument findings. Susceptibility results include, but are not limited to, susceptibility result patterns, susceptibility organism, antibiotic, susceptibility detail and susceptibility results.

In FIG. 2 at step 24, the system compares the review criteria against the patient data to determine if the patient data should be routed for review. At step 26, the clinical validation system determines if the correlation between the review criteria and the patient data is sufficient to trigger secondary review.

Figure 3:
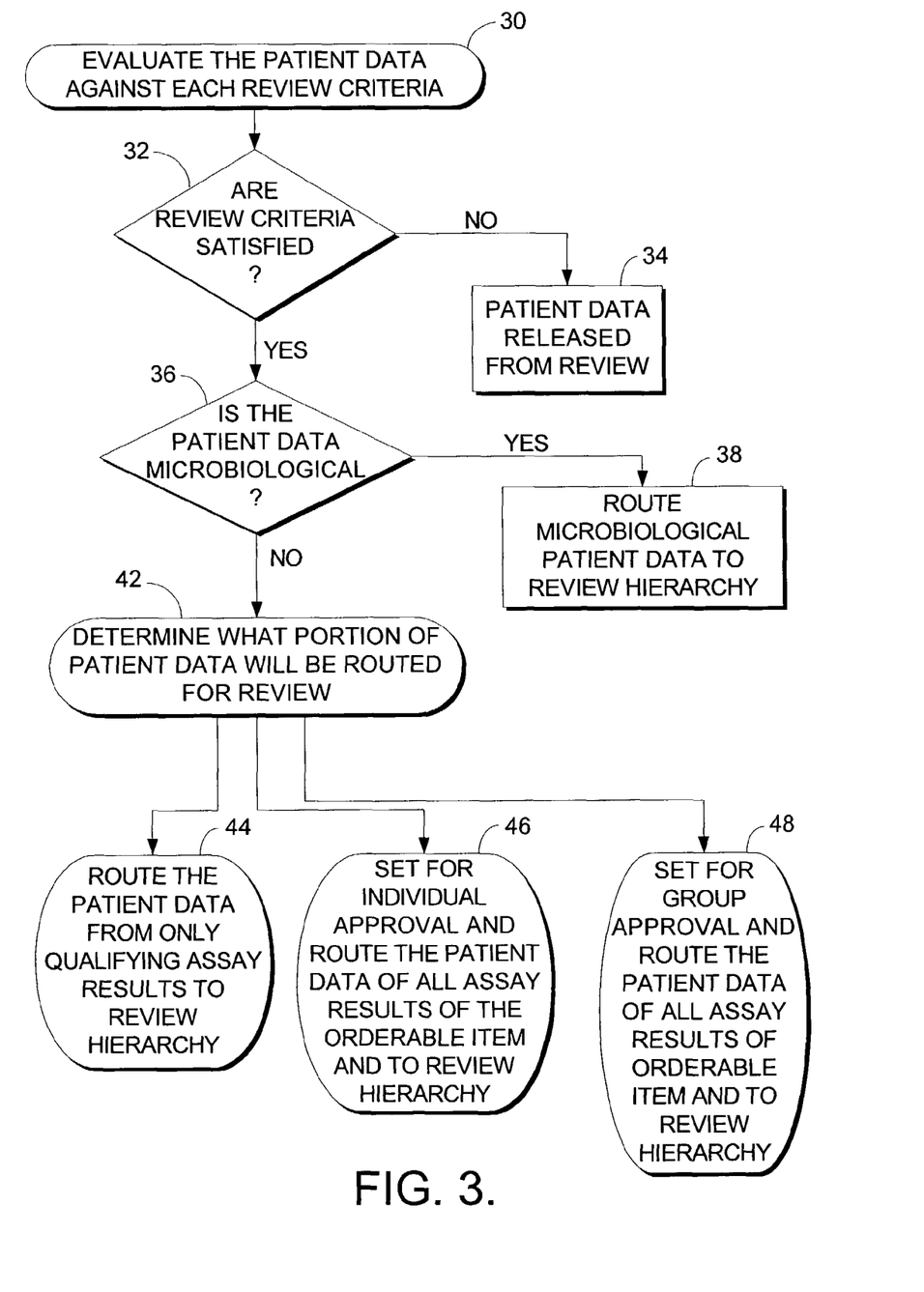
FIG. 3 is flow diagram illustrating the comparison of patient data and orders to review criteria for general laboratory test results and microbiological laboratory test results.

With reference to FIG. 3, at step 30, each type of patient data is evaluated against each of the review criteria. Preferably, at step 30, the review criteria are evaluated in their order of precedence and are typically prioritized based on importance. The order of precedence may be defined using database building tools. Next, at step 32, the clinical validation system determines if the relevant review criteria are satisfied and qualify the patient data for review (step 26 in FIG. 2). For example, if the ordering physician "Dr. Jones" is designated as a "triggering" review criteria and the patient data received by the clinical validation system indicates that Dr. Jones is the ordering physician, the patient data would qualify for review. If the review criteria are not satisfied, then the patient data is released from the system at step 34 (step 28 in FIG. 2). "Released" as used herein refers to patient data that does not require secondary review by the clinical validation system Alternatively, the clinical validation system provides a method for routing patient data manually. When the user selects to route manually, the system evaluates the review criteria first. If the patient qualifies for review, the user will be notified of the hierarchy to which the results would normally be routed. The user will have the option to select the hierarchy to which the patient data would normally be routed or the user may manually override the normal hierarchy. If the patient data does not qualify for review, the user will have the option to select a hierarchy to which the results will be routed manually.

At step 36, the system determines if the patient data to be routed is microbiological. If the patient data is microbiological than all microbiological patient data of the microbiology orderable item is routed for review if any of the microbiology patient data qualifies for review at step 38. If the system determines that the patient data is not microbiological at step 36, the clinical validation system determines what portion of the patient data that will be routed for review at step 42. Preferably, the clinical validation system routes either the patient data only of the assays that qualify the review at step 44 or the patient data of all of the assay results of the orderable item at step 46 or step 48. "Orderable item" as used herein includes the class of assays or laboratory tests that share certain attributes that are ordered together for analysis from the same sample or set of samples. For example, a CHEM-7 test is an orderable item. A CHEM-7 test is a battery of seven chemical tests ("assays") performed on blood serum or plasma. The seven tests determine the levels of blood urea nitrogen (BUN), chloride, carbon dioxide, creatinine, glucose, potassium and sodium in the sample. "Assay" as used herein includes the qualitative or quantitative analysis of a substance.

Based on the determination at step 42, the clinical validation system may also route only the patient data of the assay results that qualify for review as shown at step 44. The patient data of each individual assay result within an orderable item is evaluated for review and only the patient data of the qualifying assay results will be routed for review. For example, if the patient data of the sodium assay results of the CHEM-7 test qualifies for review, then only the patient data of the sodium assay results will be sent for review. The patient data of the other assay results of the CHEM-7 test will not be sent for review unless they qualify for review on their own.

Based on the determination at step 42, the system routes the patient data of all assay results of the orderable item at step 46. If the patient data of one assay result within an orderable item qualifies for review, then all patient data for the assay results within the orderable item is routed for review. When the system routes the patient data of all assay results at step 46, the patient data of individual assay results may be approved individually or separately. For example, if the patient data of the sodium assay results of the CHEM-7 orderable item qualifies, all other patient data for the assay results of the CHEM-7 orderable item will also be routed for review. Additionally, the different users may approve the patient data for individual assay results at different times.

Based on the determination at step 42, the system routes the patient data of all assay results for the orderable item at step 48. If the patient data of one assay result within an orderable item qualifies for review, then all patient data for assay results within the orderable item is routed for review. When the system routes the patient data of all assay results at step 48, the patient data of the individual assay results may be approved as a group. For example, one user must approve the patient data for all assay results of the orderable item at one time.

If the patient data is routed manually and the patient data would have normally triggered review, the amount and type of patient data that is routed remains the same. However, if the patient data would not have normally triggered review, and the patient data is routed manually, the patient data for the assay results of the entire orderable item is routed at step 48. As such, the patient data associated with the orderable item will have to be approved at the same time by the same user.

Referring again to FIG. 2, if the patient data qualifies for review at step 26, the patient data is routed to a review hierarchy in step 28. "Review hierarchy" as used herein is the arrangement of review queues in a sequence to facilitate the review of patient data that qualifies for review. A review hierarchy includes, but is not limited to, at least one review queue. "Review queue" as used herein is the sequence of stored result values awaiting review and approval. A review queue is defined by the user or users rather than by the work area. In other words, a review queue is a organizational tool that allows the work to be reviewed prior to verification to be organized in a manner other than assigned work area (service resource). One or more users is assigned to each review queue for monitoring, review and secondary verification.

"User" as used herein includes approvers and reviewers. "Approver" as used herein includes the person or persons who review and approve patient data. "Reviewer" as used herein includes a person or persons responsible only for reviewing the result values. The "user" may be, but is not limited to, a physician, a clinical laboratory scientist, a medical technologist, a lab technician, a pathologist, a chemist, a microbiologist, a laboratory assistant, a phlebotomist or any other person with authority to approve result values.

Figure 4:
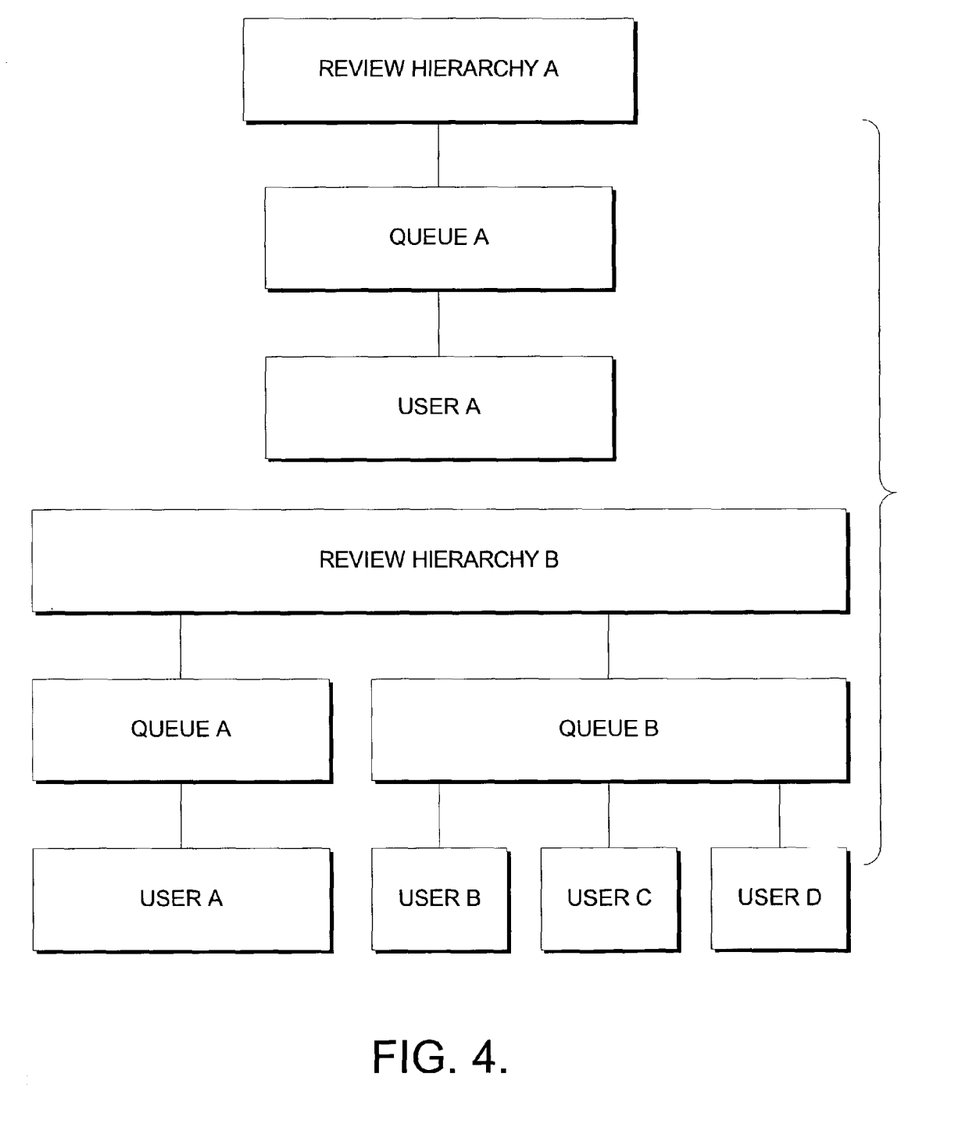
FIG. 4 is a flow diagram of two examples of review hierarchies.

FIG. 4 illustrates two review hierarchies each having at least one review queue defined by a user or group of users. Review Hierarchy A contains a Queue A that is defined by User A. On the other hand, Review Hierarchy B contains Queue A and Queue B. In Hierarchy B, Queue A is defined by User A. Queue B is defined by a group of users: User B, User C and User D. A review queue may be assigned to different hierarchies, depending on the queue and the results to be reviewed. By way of example, Queue A is defined by User A and is in both Hierarchy A and Hierarchy B.

The clinical validation system determines the review hierarchy to which the patient data should be routed by comparing the patient data against predefined qualification criteria. By way of example and not by limitation, patient data from a glucose test conducted on instrument A where the ordering physician was Dr. Jones can be routed to Hierarchy A according to predefined criteria. By way of another example, the criteria could be set to route patient data if the data is from an HLA test conducted on instrument B and ordered by Dr. Jones. One of skill in the art will appreciate that there are numerous ways to input the qualification criteria and determine the weight each of the qualification criteria is given to determine to what review hierarchy the patient data will route.

Preferably, the system organizes review queues into a hierarchy to provide a multi-level review when appropriate. Each review queue within a review hierarchy has a different level of review as set by the review criteria. For example in FIG. 4, Queue A may be the first level of review for patient data in Hierarchy B while Queue B is the final level of review for patient data. There is no limit to the number of levels of review within a hierarchy. Further, a review queue may be assigned to different hierarchies depending on the queue and the patient data to be reviewed. For example, Queue A for User A may be the first level of review for patient data in Hierarchy A but may be the final level of review for patient data in Hierarchy B.

Preferably, the clinical validation system assigns a review type when a queue is assigned to a hierarchy. A review type as used herein includes the type of approval authority designated to a review queue within a review hierarchy. One review type is a review queue that requires all users in a group to review and approve all items routed for review. This review type is only applicable to a review queue defined by a group of users. A second review type is a review queue where one user of a group is required to review and approve all items routed to that queue. A third review type is a review queue that is only for informational purposes and does not require an approval. This review type is applicable to both personal and group queues. In all instances, the system may monitor and document which users review the patient data, when the patient data is reviewed and whether the patient data was reviewed.

Figure 5:
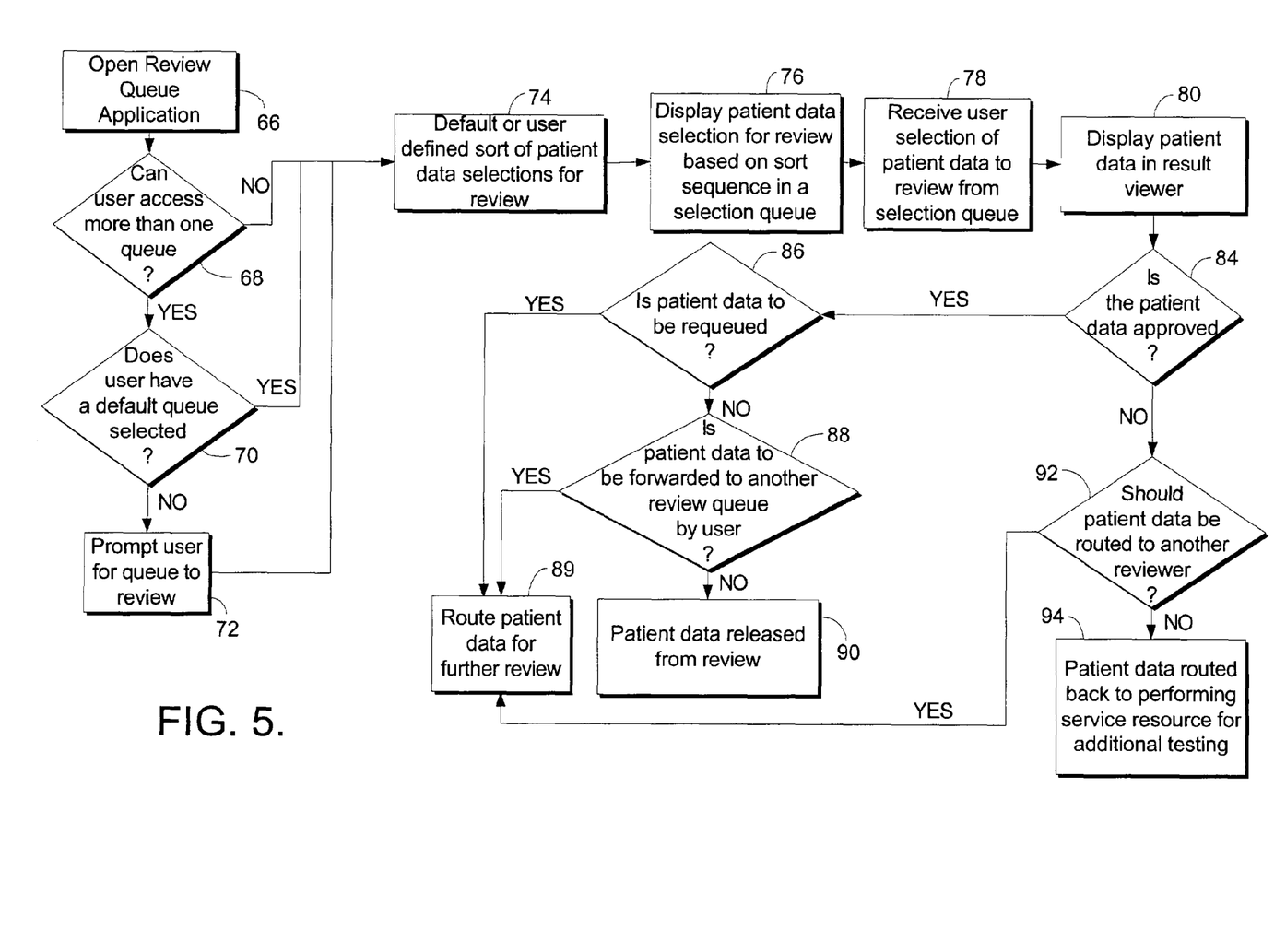
FIG. 5 is a flow diagram illustrating the review queue application.

FIG. 5 exemplifies a review queue application. At step 66, the review queue application is opened. One of skill in the art will appreciate that patient data routed for review may be accessed in a variety of other ways, including but not limited to user prompts, user menus and using data entry fields. The clinical validation system determines if the user has access to more than one queue at step 68. If the user only has access to one review queue, the system sorts the patient data selections in the review queue according to default or user defined sort criteria at step 74. If the user has access to more than one queue, the system determines if the user has a default queue selected at step 70. If the user has a default queue selected, the system sorts the patient data selections in the review queue according to default or user defined sort criteria at step 74. If the user does not have a default queue selected, the system prompts the user to select a review queue for review at step 72. After the user has selected a review queue, the system sorts the patient data selections in the selected review queue at step 74. After sorting the patient data, the system displays the patient data selections in a selection queue at step 76.

"Patient data selections" as used herein represent the patient data waiting in the review queue. Patient data selections may include, but are not limited to, the patient name, patient number, accession number, orderable item, assay, time in review, time of test, and review status. "Accession number" as used herein refers to the number used to describe an order.

Preferably, the system allows the user to define user preferences such as the default queue and sort sequence prior to displaying any patient data in the selection queue. The system will allow the user to set-up user-defined filters based on the orderable items and review statuses. If there are no previously defined user preferences, the initial sort of the review queue list will be by reporting priority, collection date and time, and then accession number.

A selection queue as used herein includes a list of patient data currently waiting in the user's personal queue. The review status of patient data is displayed in a selection queue. The review status of patient data is based on the user and their personal review status for the patient data. Preferably, review statuses include, pending prior, pending, unread and unread prior.

The "pending prior" status indicates the patient data includes results that have been routed for review and that the results are in a queue at a lower level of the hierarchy than the current user view. For example, if the current user is at Level 3 of the hierarchy and the item is in the queue for Level 1, the Level 3 user will see the status as "pending prior".

The "pending" status indicates that the order item has results that are routed for review and that are awaiting approval in the queue of the current user's view. The "unread prior" status indicates that the order item has results that have been routed for review only (and not approval) and that the results are in a queue at a lower level of the hierarchy than the current user view. The "unread" status indicates that the order item has results that are routed for review only and not approval and that are waiting to be "read" in the queue of the current user's view. The review statuses of "approved," "returned to instrument," "forwarded" and "requeued" are not available for sorting or viewing in the selection queue. "Approved" as used herein refers to the patient data that has been approved by at least one user and released from the system. "Returned to the instrument" as used herein refers to patient data that is routed to a service resource (or instrument) for further testing. "Forwarded" as used herein refers to patient data that a user forwarded to another user or review queue for review. "Requeued" as used herein refers to the patient data being placed into at least one other review queue for review.

Preferably, the user has the option to select the point in the selection queue at which they begin reviewing results. That is, if the user wishes to select patient data in the middle of the selection queue for review, they can do so. Preferably, the user also has the ability to move forward or backward in the selection queue list while reviewing results.

With continued reference to FIG. 5, after the user selects the patient data for review from the selection queue in step 78 the system presents the patient data in the result viewer for the user to view at step 80. Preferably, the patient data displayed by the result viewer is defined by user preferences. One of skill in the art will appreciate that there is a wide variety of patient data and support information that may be included in the result viewer. There is also a variety of additional patient data and support information that may be accessed from the result viewer. Preferably, the user may view support information while viewing test results.

Support information may include, but is not limited to, typing tray results, antibody screen results, gel results, blot results, HLA Haplotype chart application and crossmatch results, results for blood products, patient result values, patient current and historical ABO/Rh, transfusion requirements, blood bank patient comment indicator and comment text, patient antibodies, product number, product type (Red Cells—Adsol), product comment indicators, product attributes, product antigens, result flags, result comment indicator and comment text, normal range, personnel that "verified the result", time difference between current and previous result, and verified date and time. Preferably, the user has access to multiple previous results for that person and specific assays, access to any relevant history access to any relevant open cases, access to any relevant history and access to other lab results.

The following exemplify the types of information for general laboratory, microbiology, HLA, blood bank transfusion, blood bank donor and anatomy pathology that may be displayed in the result viewer. Preferably, for general clinical laboratory results, the system displays the most recent previous result and the patient data for individual assay result grouped at the orderable level. The system also provides the user with access to multiple previous results and access to other lab results.

Preferably, for microbiology laboratory results, the system displays microbiology reports and the susceptibility results. The system also provides a user with access to workcard results, previous microbiology results and access to all non-microbiology lab results. Preferably, for HLA laboratory test results, the system displays the patient data for each individual assay result grouped at the orderable level. The system also provides access to the HLA typing tray, antibody screen results, gel blots, crossmatch results, the HLA Haplotype chart and access to HLA history.

Preferably for blood bank transfusion results, the system displays the patient data for each individual assay result grouped at the orderable level. The system also provides the user with access to previous blood bank results/history, product information and other laboratory results. For blood bank donor, the system preferably displays the patient data for each individual assay result grouped at the orderable level. The system also provides access to previous blood bank donor results, access to donor comments and access to product information. Preferably, the system displays the anatomic pathology reports for review and any pathology alert flags for anatomic pathology. The system also provides access to relevant open cases, relevant history and to other lab results.

Figure 6:
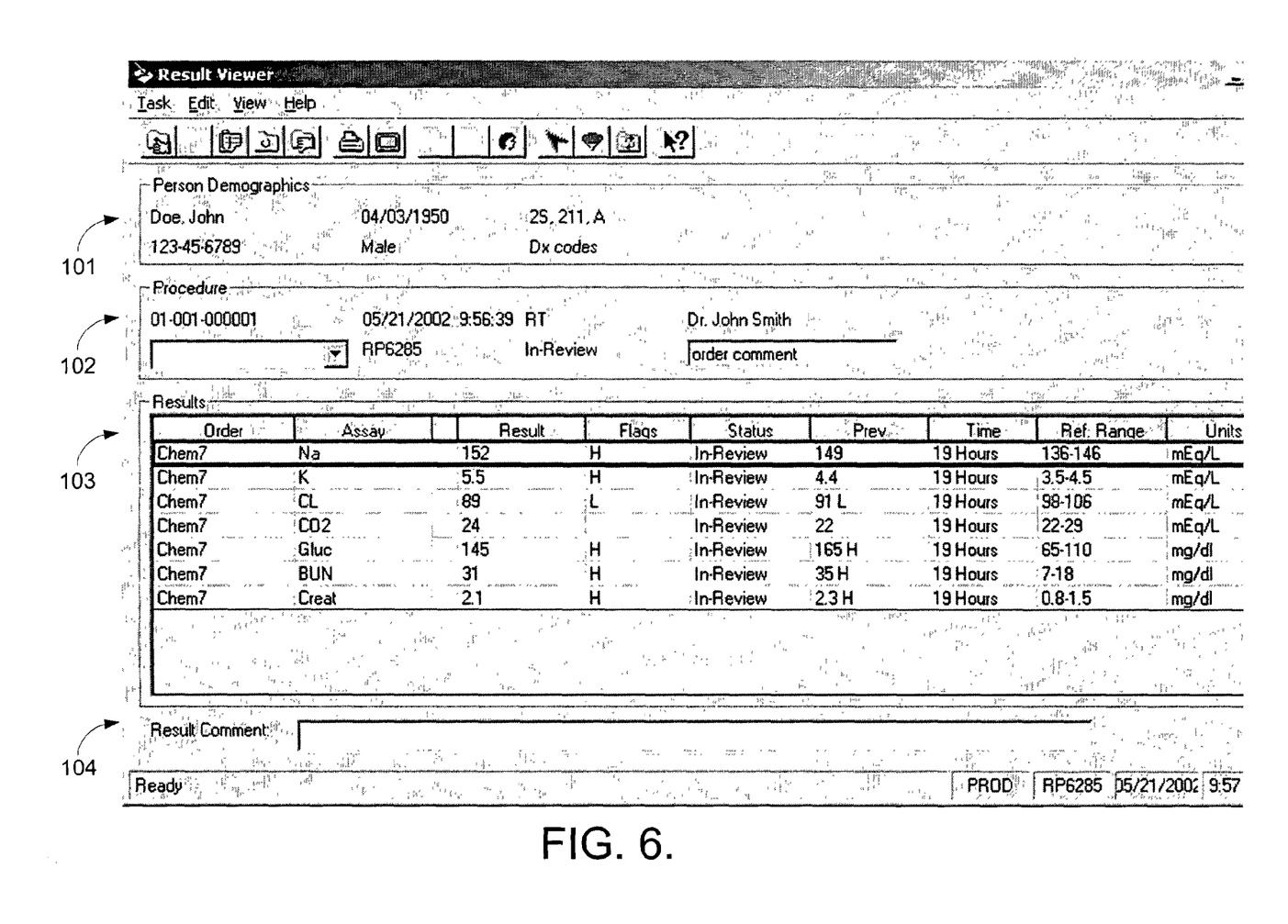
FIG. 6 is an exemplary screen of the non-microbiology clinical laboratory result viewer.

FIG. 6 illustrates a exemplary screen of a result viewer displaying non-microbiology patient data that has qualified for review. The result viewer displays person demographics 101, procedure information 102, result information 103 and an opportunity to view result comments 104. The person demographics include the patient's first and last name, date of birth, patient identifier, gender, location, ordering physician, diagnosis codes and person or comment indicators. Additionally, the system may provide the user with the ability to enter result comments when reviewing the patient data.

Procedure information 102 includes, but is not limited to, the accession number, order item name, collection date and time, person doing collection, reporting priority, order review status, and order comment. The user may access the order comment text from the procedure information.

Result information 103 includes the orderable item, the assay type, the result values, indicator flags, the review status, previous result values, time difference between the current result collection time and prior result collection time, reference ranges and units of measurement.

FIG. 7 illustrates a exemplary screen of a result viewer displaying microbiology patient data that has qualified for review. The result viewer displays person demographics 105, procedure information 106, result information 107 and susceptibility results 108. The person demographics 105 may include, but are not limited to, the patient's first and last name, date of birth, patient identifier, patient type, gender, location, ordering physician, diagnosis codes and person or comment indicators. Procedure information 106 may include, but is not limited to, the accession number, order item name, procedure type, patient medications, source body site, suspected pathogens, collection date and time, date received, start date, person doing collection, free text source and performing service resource. Result information 107 includes, but is not limited to, report name, report text, report flags, including abnormal, positive and correlation, person that "verified" the report, verified date and time. Preferably, the user has the option available to display all reports or only the latest report issues (report overlay). Susceptibility results 108 include, but are not limited to, the organism, susceptibility method, antibiotic panel, antibiotics, susceptibility details, susceptibility results, result status, person that "verified" the susceptibility, verified date and time, and susceptibility footnotes. Preferably, if there are multiple susceptibilities, they appear in the order they are displayed in the workcard. The user also has access to all workcard information for the procedure and access to previous results (both micro and non-micro) for that person.

If multiple assays on the same orderable item are routed to the same review hierarchy, the user preferably has the option to view all the assays on the same accession together, or separately by order. If only part of patient data within an orderable item are routed for review, the user preferably has the option to view all patient data of the orderable item to aid in the review process. Further, if multiple assays on the same orderable item are routed to different hierarchies for review, the user preferably has the option to view results routed to different hierarchies to aid in the review process.

Preferably, the display of patient data for review will be a display only mode. If the patient data needs to be edited, the user will have to open the appropriate function to edit the patient data. Preferably, the clinical validation system allows the user to add result or review comments during the result review and approval process. The user may add the result or review comment from the result viewer window.

Returning to FIG. 5, after the user reviews the patient data in the appropriate result viewer, at step 84 the user determines if the patient data should be approved and provides input to the system. If at step 84, the user does not approve the patient data, at step 92, the system may forward the patient data to another review queue at step 92 based on user input. If the patient data is not forwarded to another review queue at step 92, the patient data is routed back to the performing service for additional testing at step 94.

At this point, based on user input, the patient data may be requeued and placed into at least one other review queue for review at step 86, or may be forwarded the patient data to another review queue for further review at step 88. If the user decides the patient data does not require further review, the patient data is released from the review process at step 90. If the user decides the patient data requires further review at step 88, the patient data is forwarded to a review queue to be reviewed again at step 89. Preferably, the clinical validation system will update the review queue to indicate when a user is reviewing patient data, when the user has approved patient data forwarded the patient data for further review or when the patient data has been requeued.

The following exemplifies the clinical validation system in use for a non-microbiology clinical laboratory test. This example is illustrative rather than restrictive. Dr. Smith orders a CHEM-7 test to be performed on Patient A. A sample of Patient A's blood serum is taken and is sent to the chemistry clinical laboratory of the hospital for analysis. The chemistry clinical laboratory conducts a CHEM-7 test on Patient A's blood serum. As stated above, the CHEM-7 includes seven assays: a blood urea nitrogen test (BUN), a serum chloride test, a carbon dioxide test, a creatinine test, a glucose test, a serum potassium test and a serum sodium test.

With reference to FIG. 2, the result values, the order, patient information, laboratory information and miscellaneous information (collectively patient data) for the CHEM-7 test are sent from the remote computer in the chemistry clinical laboratory to the control server via the network at step 20. The patient data includes the ordering physician's name, Dr. Smith, and the presence of an error code from the performing resource of the serum sodium test. The system then accesses review criteria, previously defined using database tools, from the memory of the system at step 22. The review criteria include the presence of an error code and/or the ordering physician is Dr. Jones. If these criteria are present in the patient data, the system will trigger review of the patient data.

Turning to FIG. 3, the system compares the patient data against the review criteria at step 30 and determines if there is enough correlation between the review criteria and the patient data to trigger review at step 32. The patient data will not qualify for review based on the ordering physician review criteria, as the ordering physician of the CHEM-7 was Dr. Smith, not Dr. Jones. However, review criteria are satisfied at step 32 because of the presence of an error code from the performing resource of the serum sodium test.

The system determines that the patient data is not microbiological at step 36. The system then determines what portion of the patient data that will be routed for review at step 42. The system may either route patient data from all assay results and allow for individual approval at step 46, route patient data from all assay results and require group approval at step 48 or route patient data from only qualifying assays at step 44. In this example, the system routes patient data for all assay results and allows for individual approval at step 46. As such, not only is the serum sodium test sent for review, but also the rest of the CHEM-7 tests are routed for review.

The CHEM-7 patient data is then routed to a review hierarchy at step 46. The system determines the review hierarchy to which the patient data should be routed by comparing predefined qualification criteria to the patient data. According to the system, where the ordering physician was Dr. Smith and the patient data was from CHEM-7, the patient data is routed to the Chemistry Hierarchy.

The Chemistry Hierarchy includes two review queues, Queue A and Queue B. Queue A is defined by User A. Queue B is defined by User B and User C. The patient data routes to Queue A for information purposes only. As such, User A can review the patient data, but cannot approve the patient data. Queue B requires only one user of Queue B to approve the patient data. Thus, either User B or User C may approve the patient data.

The review queue application is opened at step 66. In this example, User B has access to both Chemistry Queue B and the Hematology Queue at step 68. At step 70, User B has selected Chemistry Queue B as the default queue. As such, at step 74, the system sorts the patient data selections in the Chemistry Queue B according to User B's defined sort criteria. The system displays the patient data selections in a selection queue at step 76. The selection queue for the Chemistry Queue B lists three patient data selections, Patient A, Patient B, Patient C. User B's sort criteria places the patient data with the earliest collection, Patient A, at the front of the selection queue. The selection queue indicates that review status for Patient A's data is "pending" and awaiting approval in User B's current view.

The system receives User B's selection of Patient A's data for review from the selection queue at step 78 and the patient data for Patient A is displayed in the result viewer at step 80 and as illustrated in FIG. 6. With reference to FIG. 6, according to User B's predefined preferences, the result viewer lists the person demographics 101 such as patient name, patient number, date of birth and patient gender at the top of the viewer. Below, the result viewer lists procedure information 102 such as the accession number, order time, review status, and ordering physician.

The results 103 of the CHEM-7 are listed below the procedure information. The serum sodium test, the assay that qualified for review, is listed first. The other assays of the CHEM-7 are listed below. According to User B's predefined preferences for column sequence, the orderable item is listed first, followed by the assay, the result, flags (if any), the review status, the prior patient result, the difference between the current result collection time and the prior result collection time, reference range and units. Below the results 103, User B may view result comments in the result comment box 104. User B also has access to patient histories and support information from the result viewer.

With reference back to FIG. 5, after reviewing the patient data in the result viewer, User B inputs approval of the patient data. Due to user input, the patient data is not requeued at step 86 and is not forwarded by the user to another review queue at step 88. As such, the patient data is released from the system at step 90. The system updates the review queue to show that Patient A's data has been approved and released from the system.

The following exemplifies the clinical validation system in use for microbiology clinical laboratory test. This example is illustrative rather than restrictive. Dr. Luden orders a culture on wound tissue taken from Patient A. A sample of Patient A's wound tissue is sent to the microbiology clinical laboratory of the hospital for analysis. The microbiology clinical laboratory conducts a culture on Patient A's wound tissue, where susceptibility results and a preliminary report are "verified."

With reference to FIG. 2, the result values, the order, patient information, laboratory information and miscellaneous information (collectively patient data) for the culture are sent from the remote computer at step 20 in the chemistry clinical laboratory to the control server via the network. The patient data includes the ordering physician's name, Dr. Luden, and abnormal results from the preliminary report and susceptibility.

The system then accesses review criteria, previously defined using database tools, from the memory of the system at step 22. In this example, review criteria include the presence of abnormal results and/or the ordering physician is Dr. Luden. If these criteria are present in the patient data, the system will trigger review of the patient data.

With reference to FIG. 3, the system compares the patient data against the review criteria to determine if there is enough correlation between the review criteria and the patient data to trigger review at step 30. The review criteria are satisfied at step 32 because there is a presence of abnormal results and the ordering physician is Dr. Luden. The system determines the patient data is microbiological at step 36 and routes the microbiological patient data the review hierarchy at step 38. The system routes the patient data for the entire orderable item.

The patient data is routed to a review hierarchy at step 28. The system determines to which review hierarchy the patient data should be routed by comparing predefined qualification criteria to the patient data. According to the system, where the ordering physician is Dr. Luden and the patient data is from a culture of tissue from a wound injury, the patient data is routed to the Microbiology Hierarchy.

The Microbiology Hierarchy includes two review queues, Queue A and Queue B. Queue A is defined by User A. Queue B is defined by User B and User C. The patient data routes to Queue A for information purposes only. As such, User A can only review and cannot approve the patient data. Queue B requires only one user of Queue B approve the patient data. Thus, either User B or User C may approve the patient data.

The review queue application is opened at step 66. User B has access to both Microbiology Queue B and the Hematology Queue at step 68. At step 70, User B has selected Microbiology Queue B as her default queue. As such, the system sorts the patient data selections in Microbiology Queue B according to User B's defined sort criteria. The system displays the patient data selections in a selection queue at step 76. The selection queue for the Microbiology Queue B lists three patient data selections, Patient A, Patient B, and Patient C. User B's sort criteria places the patient data with the earliest collection, Patient A, at the top of the selection queue. The selection queue indicates that review status for Patient A's data is "pending" and awaiting approval in User B's current view.

The system receives User B's selection of Patient A's data for review from the selection queue and the patient data is displayed in the result viewer at step 80 and as illustrated in FIG. 7. With reference to FIG. 7, according to User B's predefined preferences, the result viewer lists the person demographics 105 such as patient name, patient number, date of birth, patient gender and provider at the top of the viewer. Below, the result viewer lists procedure information 106 such as the procedure, service resource, source, body site, pathogens, collection date, receipt date and start date.

The result report 107 of the preliminary report is listed below the procedure information and a previously issued gram stain. The result report includes the report name, report text, report flags, including abnormal, the person that "verified" the report and the verified date and time. The result viewer lists the susceptibility results 108 below the result report 107. The susceptibility results include the organism, susceptibility method, antibiotic panel, antibiotics, susceptibility details, person that verified the susceptibility, the verified date and time and footnotes. User B also has access to patient histories and support information from the result viewer.

With reference to FIG. 5, after reviewing the patient data in the result viewer, User B does not approve of the patient data at step 84 and forwards the patient data to a pathology queue for further review at step 92. The patient data is routed for further review at step 89. The system updates the review hierarchy to show that Patient A's data has been forwarded to another queue.

Although the invention has been described with reference to the preferred embodiment illustrated in the attached drawing figures, it is noted that substitutions may be made and equivalents employed herein without departing from the What the invention claimed is:

1. A computer-implemented method that is performed by a processor operatively connected to a database and that determines whether clinical laboratory results qualify for user review, the method comprising:
   receiving the clinical laboratory results that include a current test value of a patient, wherein the current test value is a result generated by performing a laboratory test on a specimen obtained from the patient;
   retrieving by the processor a prior test value of the patient that is stored in the database and that was generated prior to the current test value;
   referencing by the processor a review criteria that is stored in the database and that specifies a first test-value differential and a second test-value differential, wherein the first test-value differential applies to test values below a test-value threshold and the second test-value differential applies to test values above the test-value threshold;
   comparing by the processor the current test value and the prior test value to the test-value threshold to determine whether both the current test value and the prior test value exceed the test-value threshold;
   if both the current test value and the prior test value exceed the test-value threshold, using the second test-value differential to determine whether the current test value qualifies to be reviewed, or if both the current test value and the prior test value do not exceed the test-value threshold, using the first test-value differential to determine whether the current test value qualifies to be reviewed;
   when the current test value qualifies to be reviewed, routing the clinical laboratory results to a review hierarchy that includes a first review queue and a second review queue,
      (1) wherein the first review queue comprises a first level of review and enables a plurality of users to review the laboratory test results, and
      (2) wherein the second review queue comprises a final level of review and enables a subsequent user to review the laboratory test results;
   receiving an input from all users of the plurality of users that indicates that the clinical laboratory results are approved; and
   forwarding the clinical laboratory results to the second review queue, wherein forwarding is conditioned on all users of the plurality of users approving the clinical laboratory results.

2. The method of claim 1, wherein the laboratory test includes analyzing a blood specimen obtained from the patient to measure a quantity of a molecular entity, and wherein the current test value and the prior test value are each a respective quantity of the molecular entity.

3. The method of claim 1, wherein the laboratory test includes analyzing a blood specimen of the patient to measure a quantity of glucose, and wherein the current test value and the prior test value are each a respective quantity of glucose.

4. Computer-storage media having embodied thereon computer-readable instructions, that when executed, cause a computing system to perform a method of determining whether clinical laboratory results qualify for user review, the method comprising:
   receiving the clinical laboratory results that include a current test value of a patient, wherein the current test value is a result generated by performing a laboratory test on a specimen obtained from the patient;
   retrieving by the processor a prior test value of the patient that is stored in the database and that was generated prior to the current test value;
   referencing by the processor a review criteria that is stored in the database and that specifies a first test-value differential and a second test-value differential, wherein the first test-value differential applies to test values below a test-value threshold and the second test-value differential applies to test values above the test-value threshold;
   comparing by the processor the current test value and the prior test value to the test-value threshold to determine whether both the current test value and the prior test value exceed the test-value threshold;
   if both the current test value and the prior test value exceed the test-value threshold, using the second test-value differential to determine whether the current test value qualifies to be reviewed, or if both the current test value and the prior test value do not exceed the test-value threshold, using the first test-value differential to determine whether the current test value qualifies to be reviewed;
   when the current test value qualifies to be reviewed, routing the clinical laboratory results to a review hierarchy that includes a first review queue and a second review queue,
      (1) wherein the first review queue comprises a first level of review and enables a plurality of users to review the laboratory test results, and
      (2) wherein the second review queue comprises a final level of review and enables a subsequent user to review the laboratory test results;
   receiving an input from all users of the plurality of users that indicates that the clinical laboratory results are approved; and
   forwarding the clinical laboratory results to the second review queue, wherein forwarding is conditioned on all users of the plurality of users approving the clinical laboratory results.

* * * * *